United States Patent
Belisle et al.

(10) Patent No.: US 10,555,807 B2
(45) Date of Patent: Feb. 11, 2020

(54) INTRAOCULAR LENS DELIVERY DEVICE WITH TELESCOPING PLUNGER

(71) Applicant: Novartis AG, Basel (CH)

(72) Inventors: Chris Belisle, Somerset, WI (US); Kyle Brown, Fort Worth, TX (US); Asif Fayyaz, Euless, TX (US); Jian Liu, Keller, TX (US)

(73) Assignee: Novartis AG, Basel (CH)

( * ) Notice: Subject to any disclaimer, the term of this patent is extended or adjusted under 35 U.S.C. 154(b) by 382 days.

(21) Appl. No.: 15/354,265

(22) Filed: Nov. 17, 2016

(65) Prior Publication Data

US 2017/0367817 A1    Dec. 28, 2017

Related U.S. Application Data

(60) Provisional application No. 62/375,808, filed on Aug. 16, 2016, provisional application No. 62/354,278, filed on Jun. 24, 2016.

(51) Int. Cl.
*A61F 2/16* (2006.01)

(52) U.S. Cl.
CPC .................. *A61F 2/1672* (2013.01)

(58) Field of Classification Search
CPC ............ A61F 2/1672; A61F 2002/1681; A61F 2002/1678; A61F 2002/1675; A61F 2002/167; A61F 2002/1667; A61F 2002/1662; A61F 2002/1672; A61M 5/3205; A61M 5/20; A61M 5/178; A61M 5/30; A61M 5/14; A61M 3/00
See application file for complete search history.

(56) References Cited

U.S. PATENT DOCUMENTS

| | | | |
|---|---|---|---|
| 5,947,976 | A | 9/1999 | Van Noy et al. |
| 6,010,510 | A | 1/2000 | Brown et al. |
| 6,083,231 | A | 7/2000 | Van Noy et al. |
| 6,143,001 | A | 11/2000 | Brown et al. |
| 6,537,283 | B2 | 3/2003 | Van Noy |
| 8,377,076 | B2 | 2/2013 | Downer et al. |
| 8,690,941 | B2 | 4/2014 | Downer |
| 8,894,664 | B2 | 11/2014 | Downer |
| 8,900,249 | B2 | 12/2014 | Boukhny et al. |
| 8,961,531 | B2 | 2/2015 | Brown et al. |
| 9,226,819 | B2 | 1/2016 | Downer |
| 2003/0036765 | A1 | 2/2003 | Van Noy |
| 2007/0052923 | A1* | 3/2007 | Ayyagari .............. A61F 2/1664 351/159.73 |

(Continued)

FOREIGN PATENT DOCUMENTS

| | | |
|---|---|---|
| EP | 2060243 A1 | 5/2009 |
| WO | 02074202 A1 | 9/2002 |
| WO | 2011086418 A2 | 7/2011 |

*Primary Examiner* — Erich G Herbermann (57) ABSTRACT

An intraocular lens (IOL) insertion apparatus may include a hand piece body having a distal tip, an IOL folding chamber, and IOL a dwell position, and a telescoping plunger having a first plunger portion and a second plunger portion. The first plunger portion and second plunger portion may be arranged to simultaneously advance through a first portion of a displacement of the telescoping plunger, and one of the first and second plunger portions may be arranged to advance through a second portion of the displacement of the telescoping plunger.

14 Claims, 8 Drawing Sheets

(56) References Cited

U.S. PATENT DOCUMENTS

| | | | |
|---|---|---|---|
| 2008/0027461 A1* | 1/2008 | Vaquero | A61F 2/1664 606/107 |
| 2008/0097460 A1 | 4/2008 | Boukhny et al. | |
| 2008/0200920 A1 | 8/2008 | Downer | |
| 2008/0200921 A1 | 8/2008 | Downer | |
| 2008/0221584 A1 | 9/2008 | Downer | |
| 2008/0221585 A1 | 9/2008 | Downer | |
| 2008/0255577 A1 | 10/2008 | Downer et al. | |
| 2010/0125278 A1* | 5/2010 | Wagner | A61F 2/1662 606/107 |
| 2012/0158007 A1 | 6/2012 | Brown et al. | |
| 2014/0257315 A1 | 9/2014 | Wu | |
| 2014/0303637 A1 | 10/2014 | Downer et al. | |

* cited by examiner

INTRAOCULAR LENS DELIVERY DEVICE WITH TELESCOPING PLUNGER

CROSS-REFERENCE TO RELATED APPLICATION

This application claims the benefit of U.S. Provisional Application No. 62/354,278, filed Jun. 24, 2016, and U.S. Provisional Application No. 62/375,808, filed Aug. 16, 2016, the contents of both being incorporated herein by reference.

TECHNICAL FIELD

The present disclosure is directed to methods and systems for performing ophthalmic surgical procedures, and more particularly, to methods and systems for advancing and deploying an intraocular lens during an ophthalmic surgical procedure using a telescoping plunger.

BACKGROUND

The human eye, in simple terms, functions to provide vision by refracting light passing through a clear outer portion called the cornea and focusing the light by way of the lens onto the retina at the back of the eye. The quality of the visual image created by the focused light depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the natural lens and implantation of an artificial lens, typically termed an intraocular lens (IOL).

IOLs are typically introduced into a patient's eye using an IOL insertion tool. A conventional IOL insertion tool includes an IOL insertion cartridge that may fold and insert the IOL through a relatively small incision into the eye. Particularly, the IOL cartridge may include a folding chamber that has walls shaped to cause the IOL to fold as desired as the IOL advances through the chamber. A plunger typically engages the IOL, pushes the IOL through the folding chamber, and through an incision formed in the eye.

SUMMARY

The present disclosure describes an IOL insertion apparatus that may include a hand piece body having a distal tip and a lumen formed within the hand piece body. The lumen may include a folding chamber and a dwell position. The insertion apparatus may also include a telescoping plunger moveable within the lumen over a selected distance. The telescoping plunger may include a first plunger portion and a second plunger portion. The first plunger portion and the second plunger portion may be coupled together to simultaneously advance toward the distal tip during a first portion of the selected distance and the second plunger portion being decoupled at a position along the selected distance such that only one of the first plunger portion and the second plunger portion is advanced during a second portion of the selected distance. In some aspects, only one of the first and second plunger portions may be arranged to advance during a second portion of an IOL insertion procedure.

In some implementations, the first plunger portion may include a first distal tip and the second plunger portion may include a second distal tip. The first and second distal tips may cooperate to simultaneously engage an IOL during the first portion of the selected distance. The first plunger portion and second plunger portions may be interlocked in a manner preventing lateral separation of the first plunger portion and the second plunger portion in at least one direction. Some implementations may include a mechanical stop that prevents advancement of one of the first plunger portion and second plunger portion during the second portion of the selected distance. The first plunger portion may include a first rigid elongated portion having a first length. The second plunger portion may include a second rigid elongated portion having a second length, and the second length may be is greater than the first length.

The first plunger portion may include a first rigid elongated portion and a first actuation engagement portion, and the second plunger portion may include a second rigid elongated portion and a second actuation engagement portion. The second engagement portion may contact the first actuation engagement portion at a position during displacement of the second plunger portion to prevent further displacement of the second plunger portion. Some implementations may include a coupler selectively connecting the first plunger portion and second plunger portions for simultaneous advancement through the first portion of the selected distance. The coupler may be a pin. The first plunger portion may also include a first distal tip having a first projection extending distally therefrom to engage an IOL, and the second plunger portion may also include a second distal tip having a second projection extending distally therefrom to engage the IOL. The IOL insertion apparatus may also include a pocket configured to engage and receive the IOL. The pocket may be formed in one of the first distal tip or the second distal tip. In some instances, the pocket may be formed in a combination of the first distal tip and the second distal tip.

The present disclosure also describes an IOL insertion apparatus that includes an IOL folding chamber configured to fold an IOL as the IOL is advanced therethrough, a distal tip, and a telescoping plunger configured to push an IOL toward the distal tip. The telescoping plunger may include a first plunger portion that includes a first rigid elongated portion with a distal tip operable to engage with and push an IOL through the folding chamber. The telescoping plunger may also include a second plunger portion having a second rigid elongated portion disposed adjacent to and in sliding contact with the first rigid elongated portion. The first rigid elongated portion and second rigid elongated portion may be selectively operable to move simultaneously toward the distal tip during a first portion of procedure stroke of the telescoping plunger. In some implementations, one of the first rigid elongated portion and second rigid elongated portion may be selectively operable to move independently toward the distal tip during a second portion of the stroke of the telescoping plunger.

The first plunger portion may include a first distal tip. The second plunger portion may include a second distal tip, and the first distal tip and second distal tip may align to simultaneously engage in IOL during the first portion of the stroke of the telescoping plunger. The first plunger portion and second plunger portion may be interlocked in a manner preventing lateral separation of the first plunger portion and the second plunger portion in at least one direction. The IOL insertion apparatus may include a mechanical stop configured to prevent advancement of one of the first plunger portion and second plunger portion during the second portion of the stroke of the telescoping plunger. The first plunger portion may include a first rigid elongated portion having a first length. The second plunger portion may include a second rigid elongated portion having a second length, and the second length may be greater than the first length. The IOL insertion apparatus may also include a coupler selectively connecting the first plunger portion and second plunger portions for simultaneous advancement of the first plunger portion and the second plunger portion through the first portion of the stroke of the telescoping plunger.

In some implementations, the present disclosure is directed to methods that may include engaging an IOL with a plunger having a first plunger portion and a second plunger portion. The IOL may be displaced toward a distal end of an IOL insertion apparatus by simultaneously advancing the first plunger portion and the second plunger portion. The IOL may be displaced toward a distal end of the IOL insertion apparatus by advancing only one of the first plunger portion and the second plunger portion.

In some aspects, engaging the IOL with a plunger includes simultaneously contacting the IOL with a distal end of the first plunger portion and a distal end of the second plunger portion. In some aspects the method may include folding the IOL while simultaneously advancing the first plunger portion and the second plunger portion. In some aspects, the method may include deploying the IOL while advancing only one of the first plunger portion and the second plunger portion.

BRIEF DESCRIPTION OF THE DRAWINGS

The accompanying drawings illustrate implementations of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

According to principles described herein, IOL insertion apparatuses may include a single plunger to advance an IOL through both an advancement stage and a deployment stage of IOL implantation. In some implementations, the single plunger is a telescoping plunger including an advancement portion and a deployment portion. During the advancement stage, both of the advancement portion and the deployment portion may cooperate to advance the IOL through the IOL insertion apparatus. This may include, for example, advancing the IOL through a folding chamber in the IOL insertion apparatus to a dwell position. At the dwell position, the advancement portion may halt its forward advancement, and the deployment portion may continue to advance and push the now-folded IOL from the dwell position and out an end of the IOL insertion apparatus. Because a single plunger having both an advancement portion and a deployment portion may be used for both the advancement stage and deployment stage of IOL implementation, the surgical technique may be simplified, and surgical procedures may be made more efficient for micro-incisions. Some implementations permit users to advance and deploy an IOL using only a single hand. This may allow a user to use his or her other hand to perform other tasks needed during the procedure.

Figure 1:
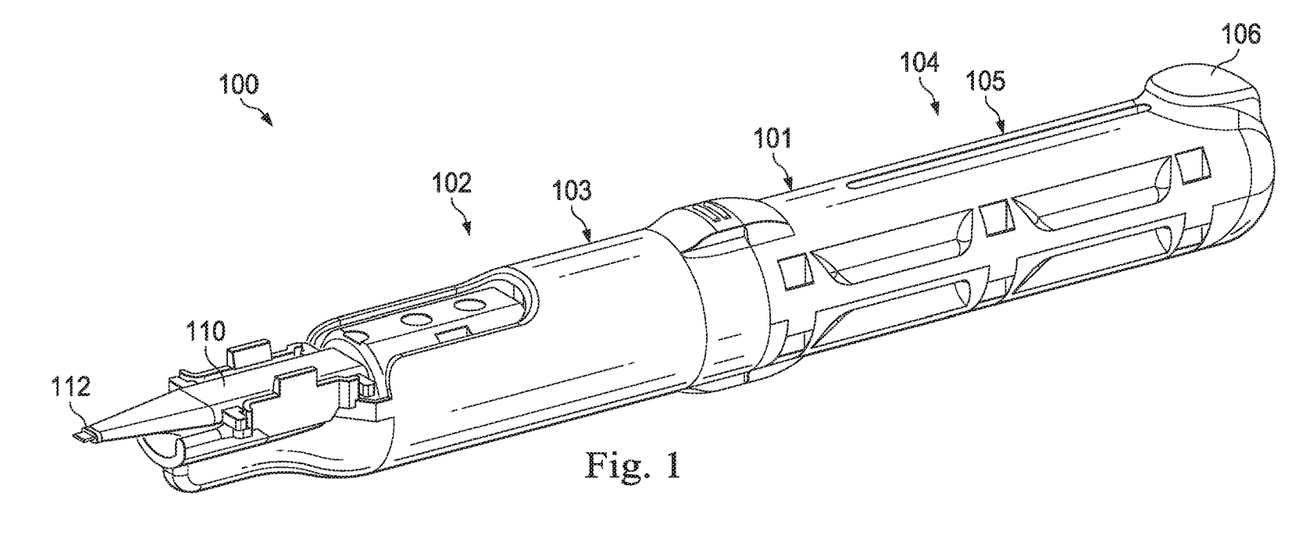
FIG. 1 is a diagram showing an example IOL insertion apparatus.

FIG. 1 is a diagram showing an example IOL insertion apparatus 100 that includes a telescoping plunger. In some implementations, the telescoping plunger engages and advances in IOL through both the advancement stage and the deployment stage. In some implementations, the IOL insertion apparatus 100 provides automated advancement and automated deployment of an IOL. According to the present example, the IOL insertion apparatus 100 includes a hand piece body 101 having a distal section 102 and a proximal section 104. The distal section 102 includes a distal body portion 103 arranged and configured to receive and maintain an IOL cartridge 110. The IOL cartridge 110 includes a distal tip 112. The distal tip 112 is sized to pass through an incision in a sclera of an eye. The IOL itself is pushed through the IOL cartridge 110 and out of the distal tip 112 during the deployment stage.

In some implementations, the cartridge 110 is a detachable cartridge that may be coupled and decoupled to the distal body portion 103. However, the scope of the disclosure is not so limited. Rather, in some implementations, the cartridge or one or more features thereof, such as a folding chamber, deployment channel, and/or surface topography utilized to fold an IOL during delivery, may be integrally formed in or form a permanent part of the IOL insertion apparatus. Such implementations may be particularly suited for preloaded IOL insertion apparatus that have an IOL contained within the IOL insertion apparatus at the time of delivery to an end user, such as a surgeon.

The proximal section 104 of the hand piece body 101 includes a proximal body portion 105. In this implementation, the IOL insertion apparatus 100 also includes an advancement trigger 106.

The hand piece body 101 is arranged to be gripped by a user. Thus, the hand piece body 101 may be ergonomically shaped for gripping by hand. In some examples, the IOL insertion apparatus 100 may be a single-use device that may be discarded after inserting an IOL into a patient's eye.

The advancement trigger 106 may be used to initiate movement of the IOL through one or both of the advancement stage and deployment stage of IOL implantation. In this particular example, the advancement trigger 106 is a release button. In some implementations, the advancement stage, which includes advancement of the IOL through the folding chamber, may be automated. In such implementations, a user may trigger the folding process by, for example, pressing the advancement trigger 106. In other implementations, the user may manually advance the IOL during either or both of the advancement stage and the deployment stage. In such implementations, a user may manually apply a force to a plunger that pushes an IOL through the hand piece body 101 for deployment in an eye of a patient.

Figure 2:
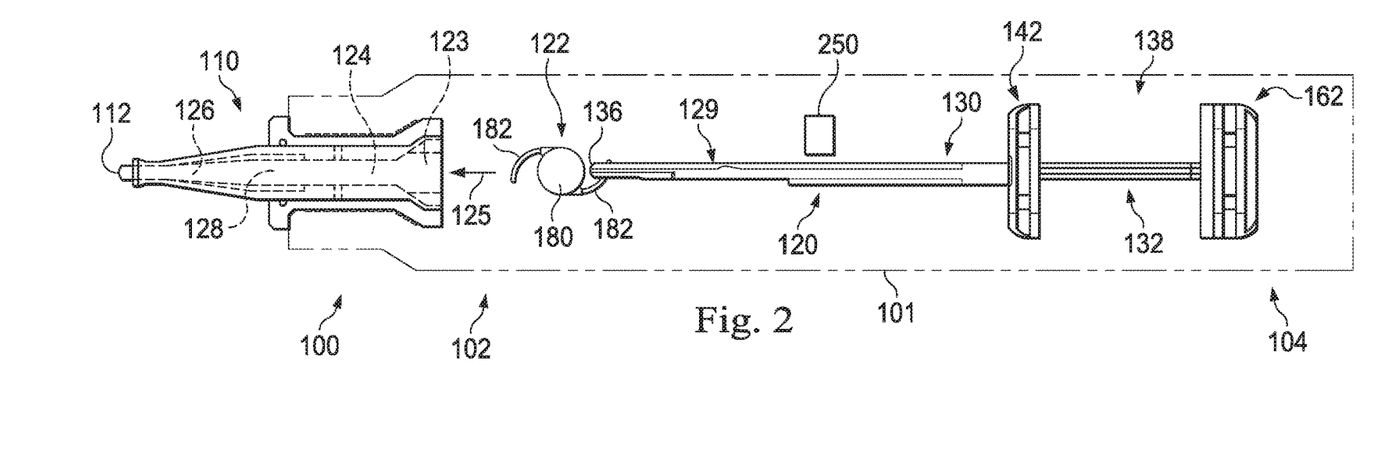
FIG. 2 is a top view of an example IOL insertion apparatus with a telescoping plunger in an initial position.
Figure 3:
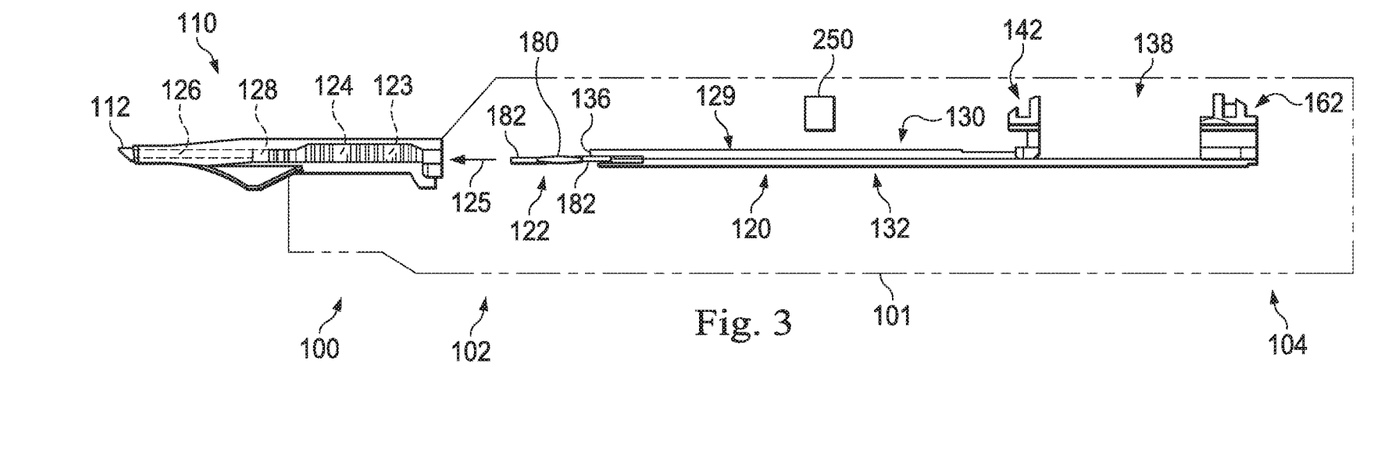
FIG. 3 is a side view of the IOL insertion apparatus shown in FIG. 2 with the telescoping plunger in the initial position.

FIGS. 2 and 3 show views of a portion of the IOL insertion apparatus 100 having a telescoping plunger 120 that may cooperate with an IOL 122 through the advancement and deployment stages. FIG. 2 shows a top view, and FIG. 3 shows a side view. These figures show an outline of the hand piece body 101 and contain therein the IOL cartridge 110, the telescoping plunger 120, and the IOL 122.

The IOL cartridge 110 forms a portion of the distal section 102 and includes a central lumen 123 including a folding chamber 124 and a deployment channel 126. As will become apparent from the description herein, the telescoping plunger 120 may advance the IOL 122 from an initial position shown in FIGS. 2 and 3 into the central lumen 123, through the folding chamber 124 to a dwell position 128, through the deployment channel 126, and out an opening in the distal tip 112.

The telescoping plunger 120 may include an advancement portion 130 and a deployment portion 132. Together, the advancement portion 130 and the deployment portion 132 cooperate to engage and push the IOL 122 in the distal direction as indicated by the arrow 125. The IOL 122 may advance into the central lumen 123 and through the folding chamber 124 to the dwell position 128. In some implementations, the advancement portion 130 may halt forward movement at the dwell position 128. The deployment portion 132 may then advance beyond the advancement portion 130 to continue to push the IOL 122 through the deployment channel 126 and out of the distal tip 112 of the IOL cartridge 110.

Figure 4:
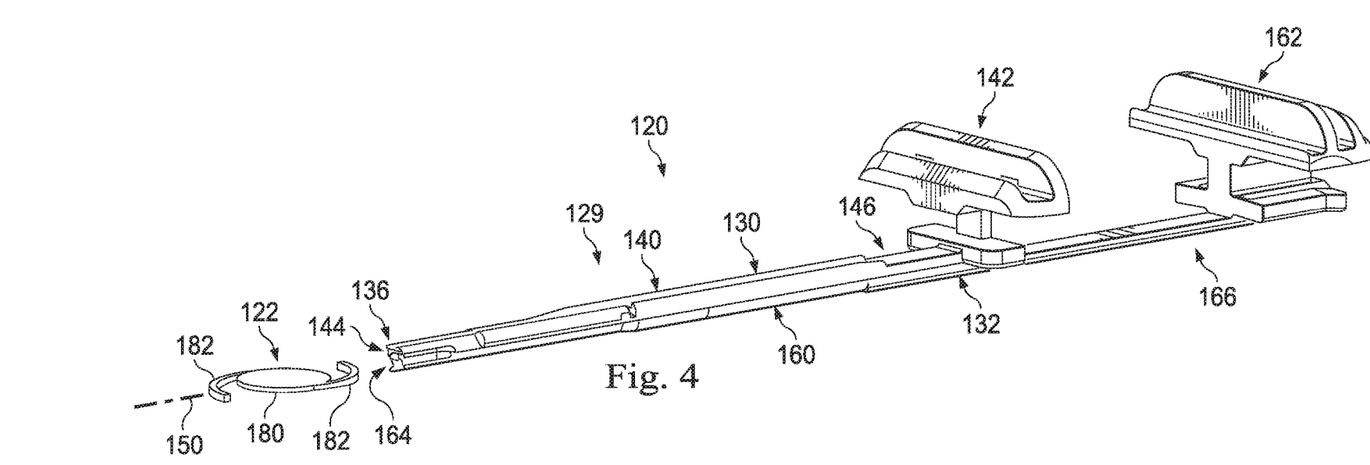
FIG. 4 is a perspective view of an example telescoping plunger and an IOL.
Figure 5:
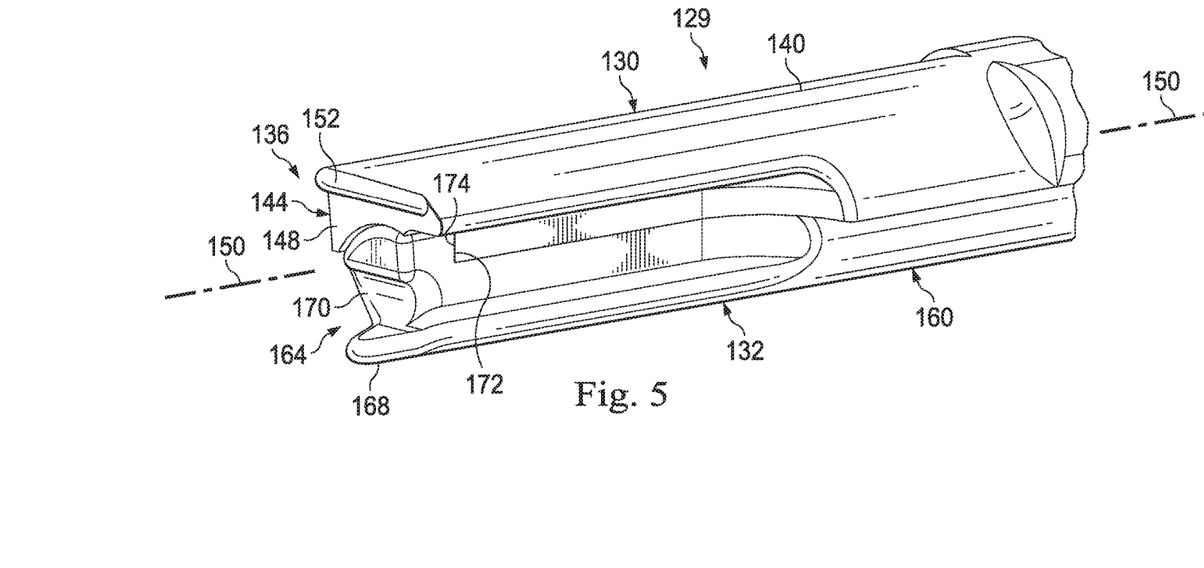
FIG. 5 is a detailed perspective view of an example tip of a telescoping plunger.
Figure 10:
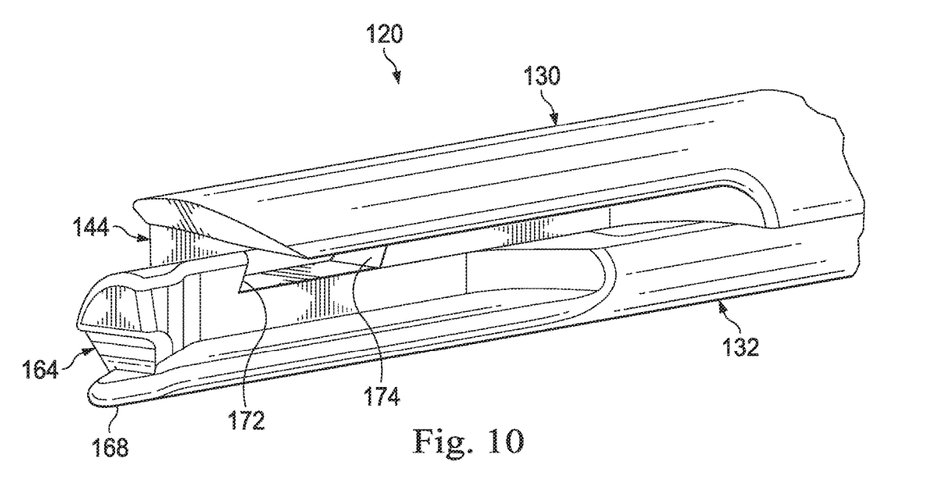
FIG. 10 is a perspective view of a tip of another example telescoping plunger in which a deployment portion of the telescoping plunger is extended beyond an advancement portion of the telescoping plunger.

FIGS. 4, 5, and 10 show the telescoping plunger 120 in greater detail. FIG. 4 shows the complete telescoping plunger 120, and FIG. 5 shows a distal tip 136 of the telescoping plunger 120. FIG. 10 shows another example telescoping plunger 120 with the deployment portion 132 extending distally beyond the advancement portion 130. The advancement portion 130 and the deployment portion 132 may be independent and separate components that cooperate together to form the telescoping plunger 120. As such, each includes individual components, but each is also used to cooperatively advance the IOL 122 through the IOL insertion apparatus 100 including the IOL cartridge 110. The advancement portion 130 and the deployment portion 132 cooperatively form a plunger shaft 129.

The advancement portion 130 has a rigid elongated portion 140 and an actuation engagement portion 142. The rigid elongated portion 140 includes a distal tip 144 and a proximal end 146. In some implementations, the distal tip 144 may be formed with a profile, ridge, or other features arranged to engage and manipulate the IOL 122. In the example shown, the distal tip 144 includes an engagement surface 148 configured to contact and engage with the IOL 122 as it advances through the folding chamber 124 of the IOL cartridge 110 shown in FIG. 2. In this implementation, the engagement surface 148 is substantially transverse to an axis 150 along the length of the plunger shaft 129. In some implementations, the engagement surface may be non-perpendicular or obliquely angled relative to the axis 150 within a range of 65 to 90 degrees, with 90 degrees being perpendicular to the axis 150. Other angles, both larger and smaller, are also contemplated. Some implementations may include an overhang 152 that may form a leading edge of the distal tip 144. The overhang 152 may cooperate with and maintain the IOL 122 in a desired position, such as directly in front of the plunger shaft 129, for advancement through the folding chamber 124 of the IOL cartridge 110.

In the exemplary implementation shown, the actuation engagement portion 142 is disposed at the proximal end 146 of the advancement portion 130. The actuation engagement portion 142 may be coupled to or driven by an actuator, a handle, or other system that may advance the actuation engagement portion 142 within the hand piece body 101 toward the distal tip 112.

The deployment portion 132 may include a rigid elongated portion 160 and an actuation engagement portion 162. As can be seen in FIG. 4, the rigid elongated portion 160 has a longitudinal length greater than a longitudinal length of the rigid elongated portion 140 forming a part of the advancement portion 130. This enables the deployment portion 132 to engage and push the IOL 122 not only during the advancement stage, but also in the deployment stage. This will become apparent in the description herein.

Similar to the rigid elongated portion 140 of the advancement portion 130, the rigid elongated portion 160 of the deployment portion 132 includes a distal tip 164 and a proximal end 166. The distal tip 164 may be formed with a surface profile having ridges or other features arranged to engage and manipulate the IOL 122 in the advancement stage and in the deployment stage. In this implementation, the distal tip 164 includes a projection shown as a bottom lip 168 and a pocket 170. The bottom lip 168 may be sized to maintain the IOL 122 in front of the distal tip 136 of the plunger shaft 129. The pocket 170 may be shaped to receive a portion of the IOL 122. The shape and or configuration of the distal tip 164 also may cooperate with walls of the folding chamber 124 in the IOL cartridge 110 to fold the IOL 122 so that it may fit through the deployment channel 126 and through a small incision during implantation in an eye. In some implementations, the pocket is formed by both the advancement portion 130 and the deployment portion 132.

In the implementation shown, the actuation engagement portion 162 is disposed at the proximal end 166 of the deployment portion 132. The actuation engagement portion 162 may be arranged to move axially in a distal direction to advance the IOL 122.

As can be seen in the arrangement of FIG. 5, the rigid elongated portion 140 and the rigid elongated portion 160 cooperate together to form the plunger shaft 129. In some implementations, the rigid elongated portions 140, 160 are simply adjacent to each other and slide or translate relative to one another along the axis 150. In other implementations, the rigid elongated portions 140, 160 are structurally engaged with each other to prevent lateral separation in at least two opposing directions. For example, some implementations include interlocking features that permit the rigid elongated portions 140, 160 to translate axially relative to one another, but restrict relative lateral movement in at least one direction. In one example, the rigid elongated portions 140, 160 are formed with tongue and groove features. In other implementations, the rigid elongated portions 140, 160 are secured relative to one another by tracks or walls formed within the hand piece body 101.

The implementation in FIG. 5 is arranged so that the advancement portion 130 may not advance forward of the deployment portion 132. In this implementation, the deployment portion 132 includes a shoulder 172 that abuts an adjacent surface 174 formed on the rigid elongated portion 140 of the advancement portion 130. The shoulder 172 contacts the adjacent surface 174 during a portion of the advancement of the telescoping plunger 120 through the IOL insertion apparatus 100. For example, in some instances, the engagement portion 142 may be driven during advancement of the IOL 122 into the dwell position 128. During this advancement of the IOL 122 into the dwell position 128, a force applied by the adjacent surface 174 to the shoulder 172 may cause the deployment portion 132 to advance simultaneously. Once the IOL 122 reaches the dwell position, a driving force applied to the engagement portion 142 may be removed, such that the deployment portion 132 may no longer be driven by the advancement portion 130. Consequently, the advancement portion 130 and the deployment portion 132 may thereafter be decoupled so that the deployment portion 132, for example, may be operable to move distally beyond the advancement portion 130. Thus, the shoulder 172 creates a physical barrier that stops or prevents the advancement portion 130 from advancing past the deployment portion 132 for a portion of the advancement of the IOL 122. In contrast, in this implementation, the deployment portion 132 may telescope beyond the advancement portion 130 to deploy the IOL 122 out of the IOL cartridge 110.

FIG. 10 shows the telescoping plunger 120 with the deployment portion 132 extending distally beyond the advancement portion. In the position illustrated, the distal tip 164 of the deployment portion 132 is located distally of the distal tip 144 of the advancement portion 130. As a result of the position of the advancement portion 130 relative to the deployment portion 132 shown in FIG. 10, a gap is formed between the shoulder 172 and the adjacent surface 174 such that the shoulder 172 and the adjacent surface 174 no longer contact each other.

Figure 11:
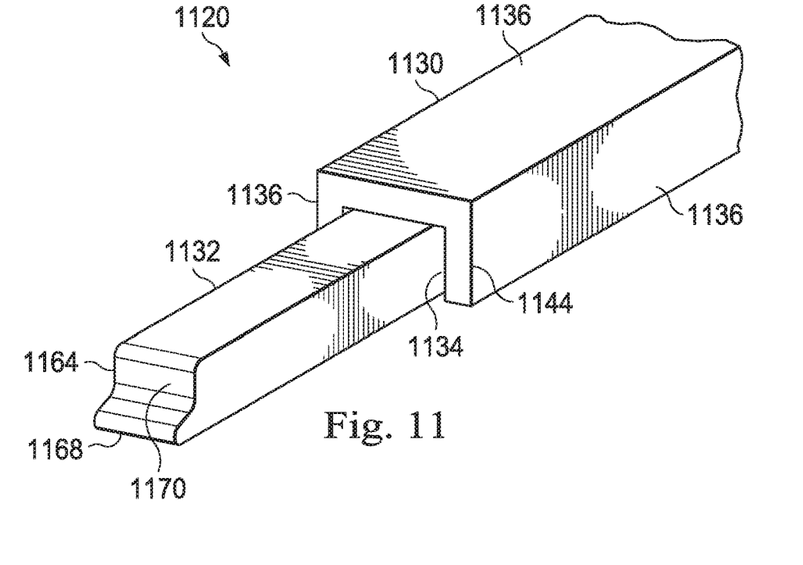
FIG. 11 is a perspective view of a distal end portion of another example telescoping plunger in which a deployment portion is shown extending distally beyond an advancement portion.
Figure 12:
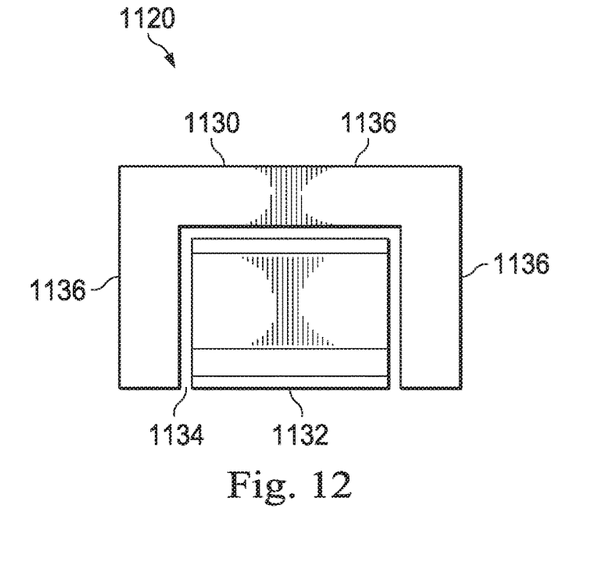
FIG. 12 is an end view of the example telescoping plunger shown in FIG. 11.

FIGS. 11 and 12 shows another example telescoping plunger 1120 that includes an advancement portion 1130 and a deployment portion 1132 telescopingly received into a groove 1134 formed in the advancement portion 1130. As arranged, the deployment portion 1132 forms a lower surface of the telescoping plunger 1120 while the sides 1136 of the advancement portion 1130 form the three other sides of the telescoping plunger 1120 when the deployment portion 1132 is fully contained within the groove 1134. Although the example telescoping plunger 1120 show that the sides 1136 have an orthogonal relationship and the groove 1134 having an orthogonal cross-section, i.e., having adjacent sides that are perpendicular to one another, the scope of the disclosure is not so limited. Rather, the cross-sectional shape of the advancement portion 1130 and deployment portion 1132 may be any desired shape. Further, the telescoping plunger 1120 may have any number of sides, and any of the sides may have any desired curvature. Accordingly, the sides 1136 and groove 1134 may have any desired shape.

The telescoping plunger 1120 may be incorporated into an IOL insertion apparatus, similar, for example, to the IOL insertion apparatus 100. Similar to the telescoping plunger 120, described herein, the advancement portion 1130 and the deployment portion 1132 cooperate to advance an IOL, which may be similar to IOL 122, through a portion of the IOL insertion apparatus. For example, as explained above, the advancement portion 1130 and the deployment portion 1132 cooperate to advance the IOL so as to place the IOL into a folded configuration. The telescoping plunger 1120 may operate to fold an IOL by, for example, advancing the IOL through a folding chamber, such as folding chamber 124, as explained above. During folding of the IOL, a distal tip 1144 of the advancement portion 1130 and a distal tip 1164 of the deployment portion align to advance the IOL through at least a portion of the IOL insertion apparatus, such as a lumen and folding chamber formed therein.

The distal tip 1144 and the distal tip 1164 may have a contour that may conform to a shape of the IOL. Further, the shapes of the distal tip 1144 and distal tip 1164 may be arranged to as to promote folding of the IOL in a particular manner. As shown in FIG. 11, the distal tip 1144 is shown as being substantially a planar surface. Further, side walls 1136 of the advancement portion 1130 are shows as being planar and being arranged orthogonally. The shape of the distal tip 1144 is shown as having a curvature that defines a bottom lip 1168 and pocket 1170. The bottom lip 1168 may be sized to maintain the entirety of the IOL distally in front of the telescoping plunger 1120. The pocket 1170 may be shaped to receive a portion of the IOL.

The scope of the disclosure is not so limited. Rather, as explained above the shape of the sides 1136 may be any desired shape. For example, the sides 1136 may be selected to produce a curved cross sectional shape of the advancement portion 1132.

Again, similar to the telescoping plunger 120, the deployment portion 1132 may advance beyond the distal tip 1144 of the advancement portion 1130 so as to deploy the folded IOL from the IOL insertion apparatus and, for example, into an eye. The advancement portion 1130 and the deployment portion 1132 may be coupled to permit both to travel together during a portion of the advancement of the telescoping plunger while also permitting the advancement portion 1130 and the deployment portion 1132 to become decoupled to permit advancement of the deployment portion 1132 beyond the advancement portion 1130 to complete delivery of an IOL.

Figure 13:
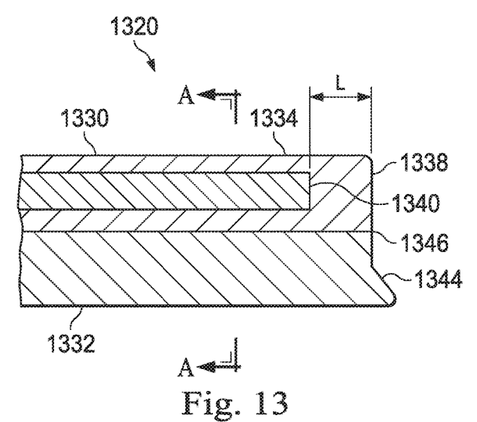
FIG. 13 is another example telescoping plunger that includes a deformable portion.
Figure 14:
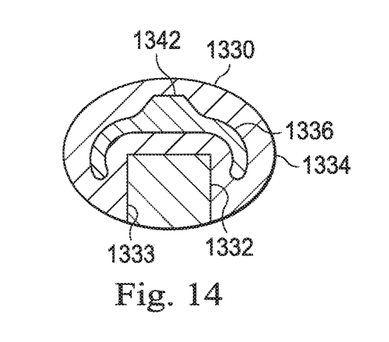
FIG. 14 is a cross-sectional view of the example telescoping plunger of FIG. 13.

FIGS. 13 and 14 illustrate another example telescoping plunger 1320. The telescoping plunger 1320 may be used in an IOL insertion apparatus, such as an IOL insertion apparatus similar to the IOL insertion apparatus 104. FIG. 13 is a cross-sectional view of the telescoping plunger 1320 taken along a longitudinally extending plane, and FIG. 14 is a transverse cross-sectional view taken along line AA. The telescoping plunger 1320 includes an advancement portion 1330 and a deployment portion 1332 telescopingly received into a groove 1333 formed in the advancement plunger 1320. As show in the illustrated example, the advancement portion 1330 surround three sides of the deployment portion 1332. The advancement portion 1330 and the deployment portion 1332 may be coupled to permit both to travel together during a portion of the advancement of the telescoping plunger while also permitting the advancement portion 1330 and the deployment portion 1332 to become decoupled to permit advancement of the deployment portion 1332 beyond the advancement portion 1330 to complete delivery of an IOL. Coupling of the advancement portion 1330 and the deployment portion 1332 may be accomplished via one or more of the manners described herein. A deformable portion 1334 of the advancement portion 1330 may be formed from a deformable material, such as silicone, for example, that is less rigid and more compressible than the material forming the deployment portion 1332. The ability of the advancement portion 1330 to deform permits the telescoping plunger 1320 to travel through a restricting central lumen, all or a portion of which may have an overall cross-sectional size that is smaller and/or has a different shape than the telescoping plunger 1320. As a result of the deformable material of the deformable portion 1334, the advancement portion 1330 is able to conform to the shape and size of the central lumen. For example, as the telescoping plunger 1320 is advanced through a constricting portion of the central lumen, the deformable portion 1334 may elongate to conform to the shape and size of the central lumen. As a result, the telescoping plunger 1320 may be used to advance an IOL through folding and deployment through a smaller incision formed in an eye, such as, for example, a sub-two millimeter incision. Similar to the other telescoping plungers described herein, once the telescoping plunger 1320 reaches a dwell position. Thereafter, the deployment portion 1332 may continue deployment of the IOL out of the IOL insertion apparatus into an eye of a patient.

In some implementations, the advancement portion 1330 may also include a backbone 1336 formed a material having a higher rigidity than the deformable portion 1334. The backbone 1336 assists in reducing binding and in maintaining an overall longitudinal shape of the telescoping plunger 1320 during operation. In some instances, the backbone 1336 may be formed from polypropylene, polycarbonate, other types of polymers, metal, or other types of rigid materials. In some instances, the deformable portion 1334 is overmolded onto the backbone 1336. In some implementations, a distal end 1338 of the deformable portion 1334 may extend a selected distance L beyond a distal end 1340 of the backbone 1336.

As shown in FIG. 14, the backbone 1336 includes a general U-shaped configuration that extends around a portion of the deployment portion 1332. The backbone 1336 may also include an enlarged central portion 1342. The shape of the backbone 1336 shown in FIGS. 13 and 14 provide rigidity and resists bending of the advancement portion 1330 and the telescoping plunger 1320 overall. However, the shape of the backbone 1336 is not limited to the example shown. Rather, in some instances, the backbone 1336 may omit the enlarged central portion 1342. In other instances, the cross-sectional shape of the backbone 1336 may not be generally U-shaped. Rather, in some instances, the backbone 1336 may have a generally planner cross-sectional shape, a generally V cross-sectional shape, or any other desired shape.

Similar to the examples described above, the advancement portion 1330 and the deployment portion 1332 cooperate to advance the IOL to the dwell position. Thereafter, the deployment portion 1332 is advanced beyond the advancement portion 1330 to deploy the IOL from the IOL insertion apparatus and into a patient's eye. As shown in FIG. 13, the deployment portion 1332 may include a bottom lip 1344. The bottom lip 1344 may be 168 may be sized to maintain the IOL in front of the distal end 1346 of the telescoping plunger 1320. In some implementations, the bottom lip 1344 may be formed in both the advancement portion 1330 and the deployment portion 1332. In other implementations, the bottom lip 1344 may be formed in only one of the advancement portion 1330 and the deployment portion 1332.

Figure 15:
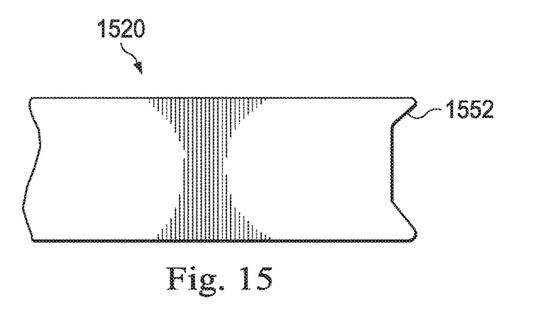
FIG. 15 shows an example of the telescoping plunger of FIG. 13 with an overhang.
Figure 16:
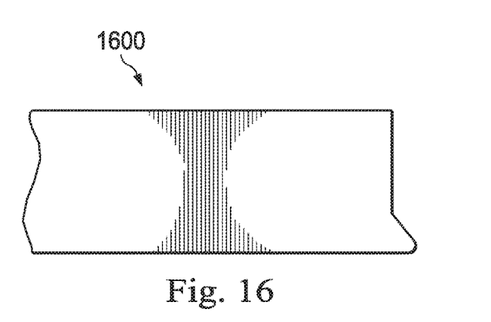
FIG. 16 shows an example of the telescoping plunger of FIG. 13 without an overhang.

FIG. 15 shows an example telescoping plunger 1520, similar to the telescoping plunger 1320, having an overhang 1552. FIG. 16 shows an example telescoping plunger 1620, similar to the telescoping plunger 1320, that omits an overhang.

In other implementations, a driving force may be applied to the deployment portion 132. For example, a driving force may be applied to the advancement portion 162 of the deployment portion 132. A coupling mechanism, such as a coupling mechanism described herein, may be employed to couple the advancement portion 130 and the deployment portion 132 through a portion of the stroke of the telescoping plunger 120. When the telescoping plunger 120 has reached a desired location, such when the IOL 122 reaches the dwell position 128, the advancement portion 130 and the deployment portion 132 may be decoupled. Because the driving force is applied to the deployment portion 132, upon decoupling, the deployment portion 132 may continue advancing the IOL 122 while the advancement portion 130 may remain at the unmoved at desired location.

Returning to FIGS. 2 and 3, the IOL 122 is shown disposed in an initial position in front of the distal tip 136 of the telescoping plunger 120. The IOL 122 includes an optic 180 and radially extending haptics 182. When the advancement portion 130 and the deployment portion 132 are coupled such that both move together during a portion of the stroke of the telescoping plunger 120, the distal tip 144 of the advancement portion 130 aligns with the distal tip 164 of the deployment portion 132 such that the distal tip 144 and distal tip 164 cooperate to advance an IOL through at least a portion of the lumen 123. Alignment of the distal tip 144 and the distal tip 164 may result in a shape of the distal tip 136 that allows the distal tip 136 to receive and/or engage with features of the IOL 122. For example, projections such as the overhang 152 and the bottom lip 168 in FIG. 5 may be arranged to project on opposing sides of the optic 180, and the pocket 170 may receive one of the haptics 182 when the telescoping plunger 120 engages and pushes the IOL 122.

FIGS. 2 and 3 show the telescoping plunger 120 in an initial position, prior to pushing the IOL 122 toward the IOL cartridge 110. Accordingly, the actuation engagement portion 142 of the advancement portion 130 is spaced apart from the actuation engagement portion 162 of the deployment portion 132. During use, the deployment portion 132 travels a greater distance than the advancement portion 130. Accordingly, in this implementation, the initial position of the actuation engagement portion 162 is spaced apart and separate from the actuation engagement portion 142.

In some implementations, the advancement portion 130 is selectively mechanically coupled to the deployment portion 132. In some examples, these are mechanically coupled via a coupler system that may use a coupler such as a fastener or a pin. Other couplers are also contemplated.

Figure 6:
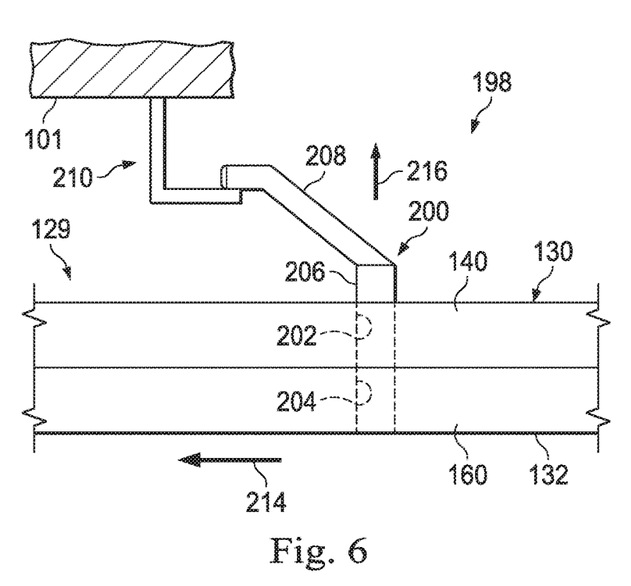
FIG. 6 is a diagram showing an example coupling system for coupling portions of a telescoping plunger.

FIG. 6 shows an example of a coupling system 198 that may be utilized to selectively couple the rigid elongated portion 140 of the advancement portion 130 to the rigid elongated portion 160 of the deployment portion 132. In this implementation, each of the rigid elongated portions 140, 160 includes a through hole 202, 204, respectively. A pin 200 is selectively receivable in the holes 202, 204. The pin 200 includes a body 206 and an arm 208. In this implementation, the arm 208 extends from the body 206 at an angle. The body 206 may fit within the holes 202, 204 and couples the rigid elongated portions 140, 160 to each other. A decoupler mechanism 210 is arranged to cooperate with the pin 200 and decouple the rigid elongated portions 140, 160 from each other. In the implementation shown, the decoupler mechanism 210 is a hook that extends from an interior of the hand piece body 101. The decoupler mechanism 210 is arranged to engage the arm 208 as the plunger shaft 129 advances in the distal direction which is indicated by the arrow 214. As the arm 208 advances distally with the plunger shaft 129, the decoupling mechanism 210 engages the angled arm 208 and causes the arm 208 to displace laterally in the direction of the arrow 216. The arm 208 raises the body 206 of the pin 200 out of the hole 204 in the rigid elongated portion 160, thereby decoupling the rigid elongated portions 140, 160 from each other.

While the coupling system 198 shown in FIG. 6 is a pin and hook system, other implementations utilize other systems and components to couple and decouple the rigid elongated portions 140, 160. Some implementations may not employ a coupling system to connect and disconnect the rigid elongated portions 140, 160. In some implementations, the decoupler mechanism 210 may be disposed within the hand piece body 101 at a location selected to decouple the rigid elongated portions 140, 160 when the distal tip 136 of the plunger shaft 129 has advanced the IOL 122 into the dwell position 128.

By being mechanically coupled, the telescoping plunger 120 may advance in a distal direction in the hand piece body 101 of the IOL insertion apparatus to advance the IOL 122 to the IOL cartridge 110. As the IOL 122 passes through the folding chamber 124 in the IOL cartridge 110, both the advancement portion 130 and the deployment portion 132 cooperate to maintain the IOL 122 in a desired orientation.

Returning to FIGS. 2 and 3, as the IOL 122 passes through the folding chamber 124, the chamber walls may force the IOL 122 to fold, giving it a smaller profile. The cooperating advancement portion 130 and deployment portion 132 continue to push the folded IOL 122 to the dwell position 128. The dwell position 128 may be a portion of the central lumen 123 having a narrower width and/or a lower height than the folding chamber 124. As such, the lumen walls at the dwell position 128 may help maintain the IOL 122 in the folded condition.

In some implementations, only the deployment portion 132 may advance distally beyond the dwell position 128. As such, some implementations are arranged to permit the advancement portion 130 and the deployment portion 132 to independently axially translate relative to one another. For example, in some implementations, the advancement portion 130 and the deployment portion 132 may advance together for a portion of the advancement of the IOL 122. Thereafter, the advancement portion 130 and the deployment portion 132 may be decoupled such that the deployment portion 132 is able to advance distally independently of the advancement portion 130. Thus, in some instances, once the advancement portion 130 and the deployment portion 132 have been advanced together to a desired point during advancement of the IOL 122, the deployment portion 132 is decoupled and able to advance further distally independently of the advancement portion 130. As the deployment portion 132 is further advanced to deliver the IOL 122 out of the distal tip 112, a position of the advancement portion 130 within the IOL insertion apparatus 100 may remain unchanged. In implementations that employ a coupler to selectively secure the advancement portion 130 to the deployment portion 132, decoupling may occur when the IOL 122 is at the dwell position 128. Decoupling may include removing the coupler from one or both of the deployment portion 132 and the advancement portion 130. For example, if the pin 200 (FIG. 6) is used to selectively couple the advancement and deployment portions 130, 132, the pin 200 may be removed either automatically or manually when the advancement portion 130 reaches the dwell position 128.

Some implementations include a mechanical stop 250 that may limit distal advancement of one or both of the advancement and deployment portions 130, 132, respectively. The mechanical stop 250 may be formed on an interior portion of the hand piece body 101. As the advancement portion 130 moves distally, it may abut against the mechanical stop 250. This hard mechanical stop 250 may prevent further distal movement of the advancement portion 130 beyond the dwell position 128. In some implementations, the mechanical stop 250 may be located to prevent further distal movement of the advancement portion 130 immediately after the advancement portion 130 is decoupled from the deployment portion 132. When the advancement portion 130 reaches its distal limit, as determined by the location of the mechanical stop 250, the deployment portion 132 may continue to advance to deploy the IOL 122 from the distal tip 112 of the IOL cartridge 110. In some implementations, the decoupling mechanism 210 of FIG. 6 is also the mechanical stop 250.

Figure 7:
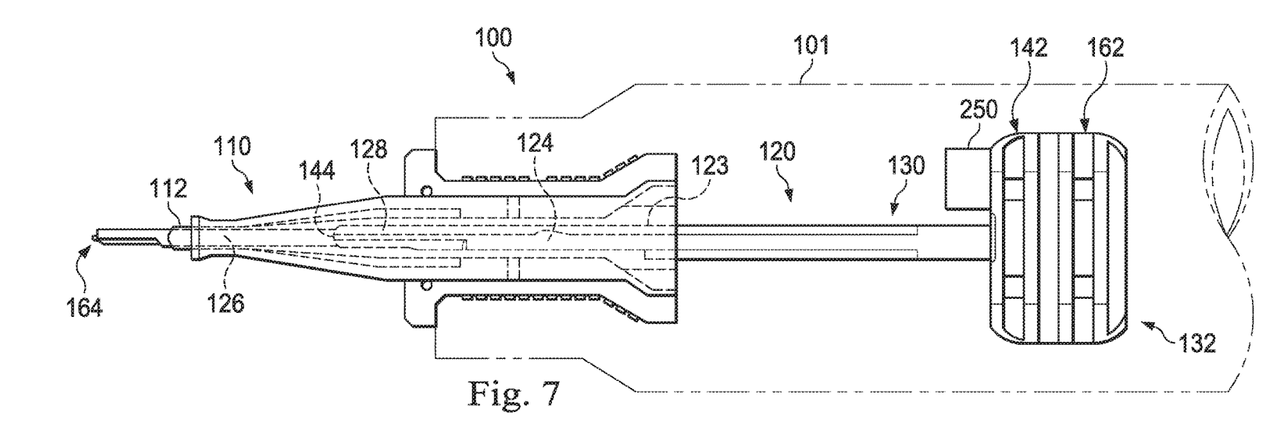
FIG. 7 is a top view of a portion of an example IOL insertion apparatus with a telescoping plunger in a final position.
Figure 8:
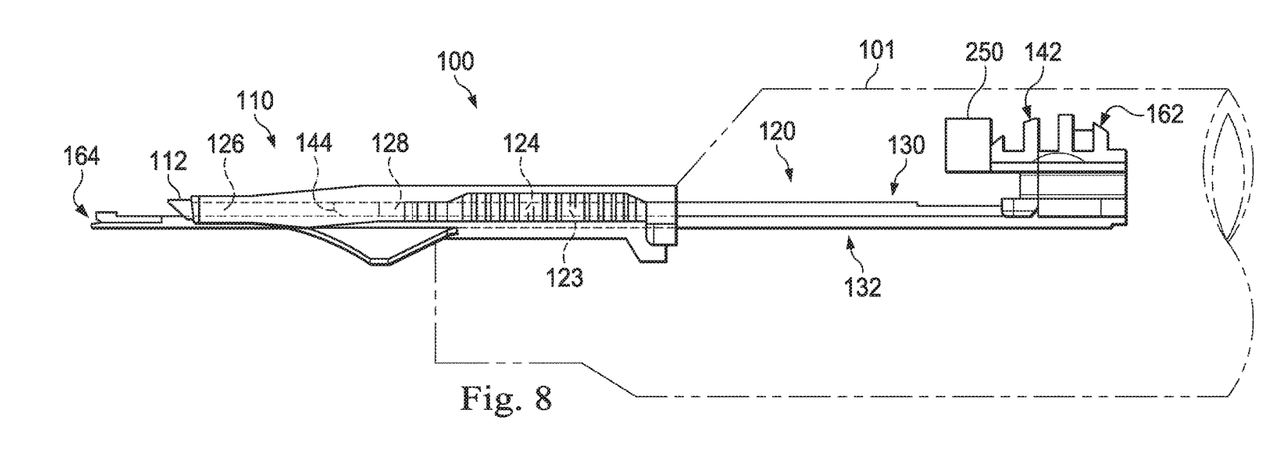
FIG. 8 is a side view of the IOL insertion apparatus shown in FIG. 7 with the telescoping plunger in the final position.

FIGS. 7 and 8 illustrate the IOL insertion apparatus 100 with the telescoping plunger 120 in a telescoped and fully deployed condition. Similar to FIGS. 2 and 3, FIGS. 7 and 8 show views of a portion of the IOL insertion apparatus 100. FIG. 7 shows a top view, and FIG. 8 shows a side view. In this state, the IOL 122 (not shown in FIGS. 7 and 8) has been deployed out of the distal tip 112 of the IOL cartridge 110. Here, the distal tip 164 of the deployment portion 132 is shown projecting out of the distal tip 112 of the IOL cartridge 110. As can be seen, the actuation engagement portion 142 is abutted against the mechanical stop 250. Accordingly, the distal tip 144 of the advancement portion 130 is disposed within the dwell position 128 of the IOL cartridge 110. In addition, the actuation engagement portion 162 of the deployment portion 132 is abutted up against actuation engagement portion 142 to the advancement portion 130. Accordingly, the deployment portion 132 is advanced to its distal limit. That is, in this implementation the actuation engagement portion 162 acts as a mechanical stop. However, other implementations operate in other manners, without the actuation engagement portions 142, 162 abutting against each other.

Because the deployment portion 132 continues to advance distally beyond the distal tip 144 of the advancement portion 130, in this example, only the deployment portion 132 travels beyond the dwell position 128 in the IOL cartridge 110. As such, the cross-sectional area, the total cross-sectional height, and/or total cross-sectional width of the telescoping plunger 120 in the deployment stage is smaller than the total cross-sectional area, the total cross-sectional height, and/or total cross-sectional width of the telescoping plunger 120 in the advancement stage. That is, in some implementations, the cross-sectional size of the deployment portion 132, transverse to the axis 150, at or near the distal end thereof is smaller than the cross-sectional size of the combination of the advancement portion 130 and deployment portion 132, transverse to the axis 150, at or near the distal end thereof. Thus, the IOL 122 may be advanced, folded, and deployed using a single plunger, while the cornea incision size may be minimized because only a portion of the full plunger actually passes through the incision. In other implementations, the advancement portion 130 may advance a distance beyond the dwell position 128.

Figure 9:
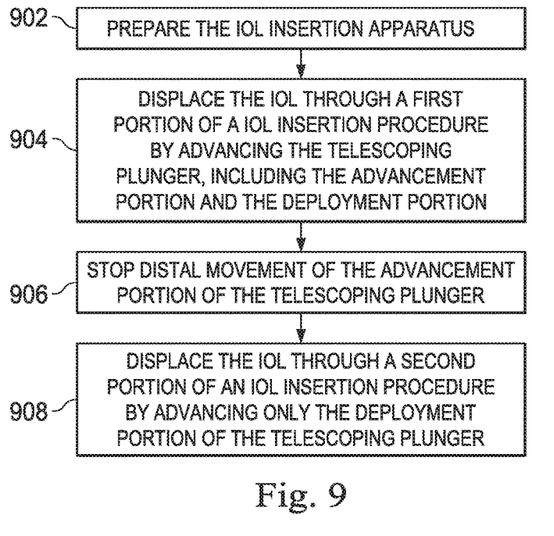
FIG. 9 is a flowchart showing an example method for using an IOL insertion apparatus that utilizes a telescoping plunger.

FIG. 9 is a flowchart showing an example method 900 of deploying an IOL using a telescoping plunger according to some implementations. The telescoping plunger may be similar to the telescoping plunger 120 described herein. According to the present example, the method 900 includes preparing the IOL insertion apparatus for use at 902. Preparing the IOL for use may involve injecting a lubricant into the folding chamber of the hand piece body. The lubricant may fill space around the IOL to provide lubrication for the IOL as it passes through the folding chamber. In some implementations, the lubricant may be an Ophthalmic Visio-surgical Device (OVD) fluid.

At 904, a user may displace the IOL through a first portion of an IOL insertion apparatus by advancing the telescoping plunger. This may correspond with an advancement stage of a surgical procedure, and may include simultaneous advancement of the advancement portion and the deployment portion of the telescoping plunger. In some implementations, advancing the telescoping plunger may include actuating an advancement trigger to advance the telescoping plunger in a hand piece body of the IOL insertion apparatus. In some implementations, this may include pressing a button on the hand piece body to actuate a drive mechanism attached to the telescoping plunger. In other implementations, this may include a user manually advancing the telescoping plunger by applying a manual load to move the telescoping plunger in the distal direction. In some implementations, the advancement portion and the deployment portion may be coupled together as discussed herein. While advancing the telescoping plunger, the distal tips of the advancement and deployment portions may both simultaneously engage the IOL. In some implementations, the distal tips of the advancement and deployment portions cooperate to maintain the IOL in a desired orientation as it passes through the folding chamber.

At 906, distal movement of the advancement portion of the telescoping plunger may be stopped. In some implementations, it may be stopped when the advancement portion engages or abuts against a mechanical hard stop. In some implementations, the advancement portion may stop distal movement when the IOL is disposed in the dwell position.

In implementations where the advancement and deployment portions, such as, for example advancement and deployment portion 130, 132, are selectively coupled, a physical structure may be used to decouple or disconnect the advancement and deployment portions. Some implementations may include removing a pin or other fastener to permit axial movement of the deployment portion relative to the advancement portion.

At 908, a user may displace the IOL through a second portion of the IOL insertion procedure by advancing the deployment portion of the telescoping plunger while preventing continued movement of the advancement portion. This may correspond to a deployment stage of a surgical procedure, and may include advancing the folded IOL from the dwell position out the distal tip of the IOL cartridge and into the eye. In some implementations, the lumen of the IOL cartridge is reduced in size towards the distal end of the cartridge. In some of these implementations, the lumen is sized such that the deployment and advancement portions of the telescoping plunger cannot simultaneously fit within the lumen. By advancing only the deployment portion, the distal tip of the IOL cartridge may be minimized, requiring only a small incision through which the distal tip, and ultimately the IOL, may be passed. In some implementations, the deployment portion may be in sliding contact with the advancement portion and may, therefore, slide along the advancement portion.

Use of methods and systems described herein may provide a number of benefits and advantages over other IOL delivery systems, such as, for example, IOL delivery systems that utilize two separate plungers to advance and deploy an IOL, respectively. In some examples, the IOL insertion apparatus 100 may be operated with the use of a single hand, freeing up the other hand for the user, such as to gain greater control of the entire surgical procedure. Another advantage may be that an incision size may be minimized, improving the safety of the surgery and possibly resulting in faster wound healing, less trauma, or other patient advantages. Implementations using automated plunger advancement may reduce risks associated with driving the plunger. As such, the speed of the IOL delivery may be more consistent and containable. Furthermore, the operation steps may be reduced compared to existing systems. For example, simplified operation steps may enable a user to reduce the overall time associated with inserting an IOL and to conduct the surgical procedure more efficiently and effectively.

Persons of ordinary skill in the art will appreciate that the encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraocular lens (IOL) insertion apparatus comprising:
    a hand piece body having a distal tip;
    a lumen formed within the hand piece body, the lumen comprising:
        a folding chamber; and
        a dwell position; and
    a telescoping plunger moveable within the lumen over a selected distance, the telescoping plunger comprising:
        a first plunger portion;
        a second plunger portion, and
        a pin coupler selectively connecting the first plunger portion and second plunger portion, wherein the first plunger portion and the second plunger portion are selectively coupled together to simultaneously advance toward the distal tip during a first portion of the selected distance, and wherein the first plunger portion and the second plunger portion being are selectively decoupled at a position along the selected distance such that only one of the first plunger portion and second plunger portion is advanced during a second portion of the selected distance.

2. The apparatus of claim 1, wherein the first plunger portion comprises a first distal tip, wherein the second plunger portion comprises a second distal tip, and wherein the first and second distal tips cooperate to simultaneously engage an IOL during the first portion of the selected distance.

3. The apparatus of claim 1, wherein the first plunger portion and second plunger portion are interlocked in a manner preventing lateral separation of the first plunger portion and the second plunger portion in at least one direction.

4. The apparatus of claim 1, further comprising a mechanical stop that prevents advancement of one of the first plunger portion and second plunger portion during the second portion of the selected distance.

5. The apparatus of claim 1, wherein the first plunger portion comprises:
   a first rigid elongated portion; and
   a first actuation engagement portion,
   wherein the second plunger portion comprises:
   a second rigid elongated portion; and
   a second actuation engagement portion, and
   wherein the second actuation engagement portion contacts the first actuation engagement portion at a position during displacement of the second plunger portion to prevent further advancement of the second plunger portion.

6. The apparatus of claim 5, wherein the first rigid elongated portion has a first length, wherein the second rigid elongated portion has a second length, and wherein the second length is greater than the first length.

7. The apparatus of claim 1, wherein the first plunger portion comprises a first distal tip having a first projection extending distally therefrom to engage an IOL, and the second plunger portion comprises a second distal tip having a second projection extending distally therefrom to engage the IOL.

8. The apparatus of claim 7, further comprising a pocket configured to engage with and receive the IOL, the pocket being formed in one of:
   the first distal tip;
   the second distal tip; and
   a combination of the first distal tip and second distal tip.

9. An intraocular lens (IOL) insertion apparatus comprising:
   an IOL folding chamber configured to fold an IOL as the IOL is advanced therethrough;
   a distal tip; and
   a telescoping plunger configured to push the IOL toward the distal tip, the telescoping plunger comprising:
      a first plunger portion comprising a first rigid elongated portion that includes a first distal plunger tip operable to engage with and push the IOL through the folding chamber; and
      a second plunger portion comprising a second rigid elongated portion disposed adjacent to and in sliding contact with the first rigid elongated portion; and
      a pin coupler selectively connecting the first plunger portion and second plunger portion, wherein the first rigid elongated portion and second rigid elongated portion are selectively operable to move simultaneously toward the distal tip during a first portion of a stroke of the telescoping plunger, and wherein one of the first rigid elongated portion and second rigid elongated portion are selectively operable to move independently toward the distal tip during a second portion of the stroke of the telescoping plunger.

10. The apparatus of claim 9, wherein the second plunger portion comprises a second distal plunger tip, and wherein the first distal plunger tip and second distal plunger tip align to simultaneously engage the IOL during the first portion of the stroke of the telescoping plunger.

11. The apparatus of claim 9, wherein the first plunger portion and second plunger portion are interlocked in a manner preventing lateral separation of the first plunger portion and the second plunger portion in at least one direction.

12. The apparatus of claim 9, comprising a mechanical stop configured to prevent advancement of one of the first plunger portion and second plunger portion during the second portion of the stroke of the telescoping plunger.

13. The apparatus of claim 9, wherein the first rigid elongated portion has a first length, wherein the second rigid elongated portion has a second length, and wherein the second length is greater than the first length.

14. The apparatus of claim 9, wherein one of the first plunger portion and the second plunger portion comprises a deformable portion.

* * * * *